US00PP32011P2

(12) United States Plant Patent
O'Connell

(10) Patent No.: US PP32,011 P2
(45) Date of Patent: Jul. 21, 2020

(54) ***PORTULACARIA* PLANT NAMED 'LILLIPUT'**

(50) Latin Name: *Portulacaria afra*
Varietal Denomination: LILLIPUT

(71) Applicant: Altman Specialty Plants, Inc, Vista, CA (US)

(72) Inventor: Renee O'Connell, Escondido, CA (US)

(73) Assignee: Altman Specialty Plants, Inc., Vista, CA (US)

( * ) Notice: Subject to any disclaimer, the term of this patent is extended or adjusted under 35 U.S.C. 154(b) by 0 days.

(21) Appl. No.: 16/501,791

(22) Filed: Jun. 6, 2019

(51) Int. Cl.
*A01H 5/12* (2018.01)
*A01H 6/00* (2018.01)

(52) U.S. Cl.
USPC ..... Plt./373

(58) Field of Classification Search
USPC ..... Plt./373
See application file for complete search history.

*Primary Examiner* — Susan McCormick Ewoldt
*Assistant Examiner* — Karen M Redden
(74) *Attorney, Agent, or Firm* — Cassandra Bright

(57) ABSTRACT

A new and distinct *Portulacaria* cultivar named 'LILLIPUT' is disclosed, characterized by a diminutive overall stature, and small emerald green leaves. Plants are a size suitable for smaller gardens. The new variety is a *Portulacaria*, typically produced as a garden or container plant.

2 Drawing Sheets

Figure 1:
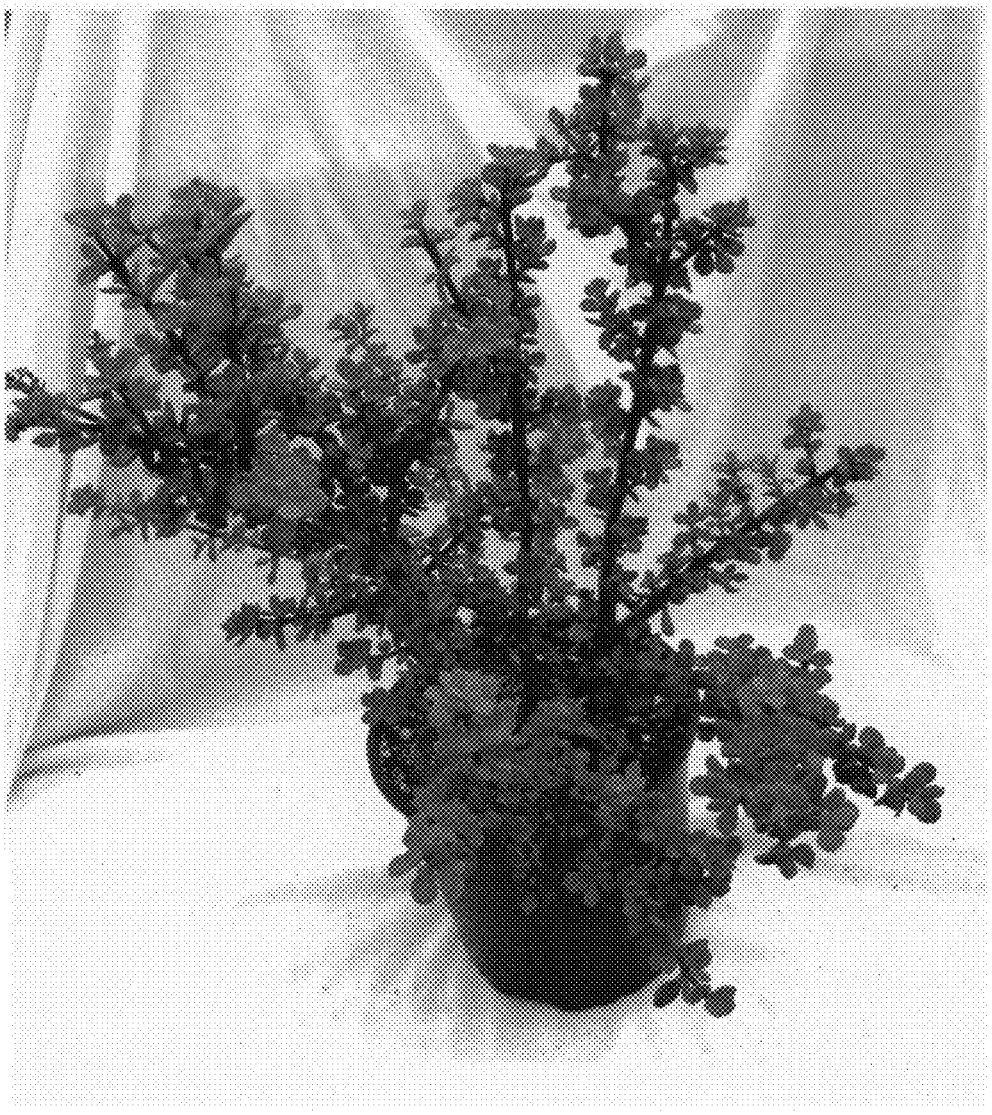

Latin name of the genus and species: *Portulacaria afra*.
Variety denomination: 'LILLIPUT'.

BACKGROUND OF THE INVENTION

The new cultivar is a product of a naturally occurring whole plant mutation in a commercial nursery in Vista, Calif. The parent is an unpatented, unnamed variety of *Portulacaria afra*. 'LILLIPUT' was found and selected by the inventor in Vista, Calif. in June 2013.

Asexual reproduction of the new cultivar 'LILLIPUT' was first performed by vegetative tip cuttings at a commercial greenhouse in Vista, Calif. in July 2013. 'LILLIPUT' has since produced at least 15 generations and has shown that the unique features of this cultivar are stable and reproduced true to type.

SUMMARY OF THE INVENTION

The cultivar 'LILLIPUT' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'LILLIPUT'. These characteristics in combination distinguish 'LILLIPUT' as a new and distinct *Portulacaria* cultivar:

1. Small overall stature.
2. Small leaves.
3. Suitable for smaller gardens.

PARENTAL COMPARISON

Plants of the new cultivar 'LILLIPUT' are similar to the parent in most horticultural characteristics. However, plants of the new variety differ from the parent in the following:

1. New variety exhibits a smaller stature than the parent.
2. New variety displays a miniature appearance, due to smaller ramification and smaller leaves than the parent. The parent is standard sized.
3. New variety is more suitable for small dish gardens than the parent.

COMMERCIAL COMPARISON

'Lilliput' can be compared to the unpatented commercial variety *Portulacaria afra* 'Prostrata'. The two *Portulacaria* varieties are similar in most horticultural characteristics; however, the new variety differs in the following:

1. New variety has smaller leaves than this comparator.
2. New variety has an upright morphology, while the comparator has a more pendulous morphology.
3. New variety is more suitable for small dish gardens than this comparator.

'Lilliput' can also be compared to the unpatented commercial variety *Portulacaria afra* 'Variegta'. The two *Portulacaria* varieties are similar in most horticultural characteristics; however, the new variety differs in the following:

1. New variety displays a more diminutive morphology than this comparator.
2. New variety exhibits much smaller leaves and ramifications than this comparator.
3. 'Lilliput' produces leaves that are monotone emerald green, whereas 'Variegta' produces mint green leaves, margined with pale yellow.

BRIEF DESCRIPTION OF THE PHOTOGRAPHS

The photographs were taken using conventional techniques and equipment. While the colors in these photographs may display variances of color as compared to the living cultivar, due to LRV (light reflectance value), they are as accurate as possible using conventional photographic techniques. Colors in the photographs may appear to differ slightly from the color values cited in the botanical description, which accurately describe the colors of new *Portulacaria afra* 'Lilliput'.

FIG. 1 illustrates in full color the rosette being described of *Portulacaria afra* 'Lilliput', grown in a greenhouse (approximately 2500 foot candles) in Vista, Calif., at approximately 1 year.

Figure 2:
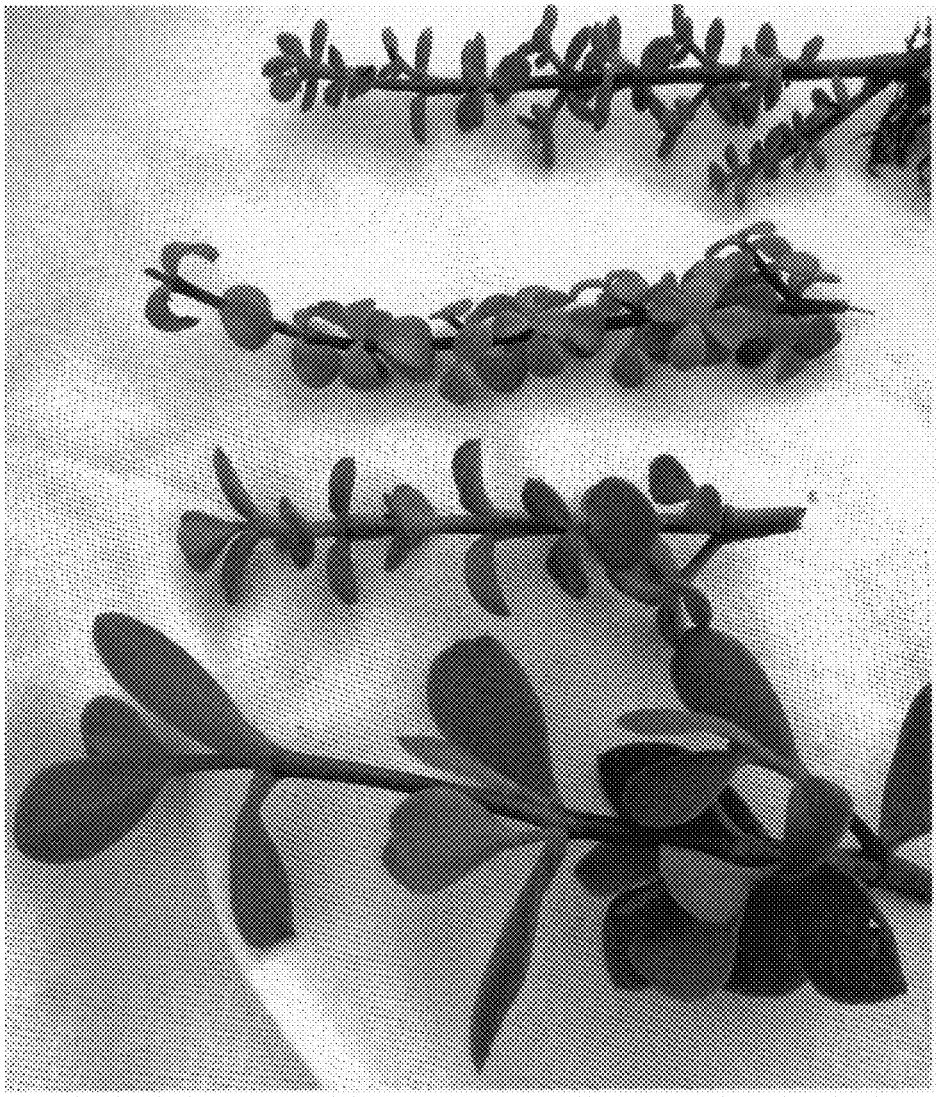

FIG. 2 illustrates in full color a comparison of stems and foliage of 4 *Portulacaria afra* varieties. On the far left is *Portulacaria afra* 'Macrophylla', next from the left *Portulacaria afra* (unnamed parent), third from the left, *Portulacaria afra* 'Prostrata'. Furthest right is *Portulacaria afra* 'Lilliput'. All plants were grown in a greenhouse (approximately 2500 foot candles) in Vista, Calif.

DETAILED BOTANICAL DESCRIPTION

In the following description, color references are made to The Royal Horticultural Society Color Chart, 2007 edition, except where general terms of ordinary dictionary significance are used. The following observations and measurements describe 'LILLIPUT' plants in a commercial shadehouse in Vista, Calif. Temperatures ranged from 34° F. to 90° F. during the night and day. No artificial light, photoperiodic treatments or chemical treatments were given to the plants. Natural light conditions were approximately 3000 to 4000 foot candles of light. Measurements and numerical values represent averages of typical plant types.

Botanical classification: *Portulacaria afra* 'LILLIPUT'.

Age of the plant described: About 1 year.

PROPAGATION

Time to initiate roots: Approximately 25 days at 22° C.

Propagation method: Vegetative tip cuttings.

PLANT

Growth habit: Tender succulent. Upright, with lateral branches occurring at angles of 15 to 85° from center. Acute angles most common.

Container size: 5 inches.

Height: Approximately 32 cm.

Plant spread: Approximately 30 cm, in a 5 inch pot.

Growth rate: Moderate.

Branching characteristics: Opposite. Each opposite pair occurring 90° from above pair.

Length of lateral branches: Average range 5 to 21 cm.

Diameter of lateral branches: Approximately 4 to 5 mm.

Quantity branches: 2 to 4 large main lateral branches, from each main stem. Upper section of main stems has 8 to 12 small lateral branches forming.

*Texture*.—Glabrous.

*Shape*.—Round.

*Color*.—Near RHS Greyed-Purple 185B.

Root description: Densely fibrous. Brown, not accurately measured with a standard color chart.

FOLIAGE

Leaf:

*Arrangement*.—Opposite Sessile.

*Average length*.—Average range 1.2 to 1.5 cm.

*Average width*.—Average range 1.1 to 1.4 cm.

*Shape of blade*.—Broad spatulate.

*Apex*.—Broad rounded, mucronate.

*Base*.—Broad taper.

*Margin*.—Entire.

*Texture of top surface*.—Glabrous.

*Texture of bottom surface*.—Glabrous.

*Appearance of top surface*.—Slightly glossy.

*Appearance of lower surface*.—Slightly glossy.

*Quantity of leaves per branch*.—Approximately 50.

*Color*.—Young foliage upper side: RHS Yellow-Green 144A. Young foliage, under side: RHS Yellow-Green 144B. Mature foliage upper side: RHS Green 138A. Mature foliage, under side: RHS Yellow-Green 144A.

*Venation*.—There is no visual appearance of venation.

FLOWER

Flowering not observed.

OTHER CHARACTERISTICS

Fruits and seeds: Not observed to date.

Temperature tolerance: USDA zones 10 and above.

Disease/pest resistance: Neither resistance nor susceptibility to standard pathogens or pests of *Portulacaria* observed.

Drought tolerance: Good tolerance for drought.

What is claimed is:

1. A new and distinct cultivar of *Portulacaria* plant named 'LILLIPUT' as herein illustrated and described.

* * * * *